US012570951B2

(12) United States Patent
Lin et al.

(10) Patent No.: US 12,570,951 B2
(45) Date of Patent: Mar. 10, 2026

(54) ALGAL BIOFILM HARVESTING METHOD CAPABLE OF REDUCING RELEASE OF PLANKTONIC MICROALGAE

(71) Applicant: Nanjing University, Nanjing (CN)

(72) Inventors: Yuan Lin, Nanjing (CN); Yanting Chen, Nanjing (CN); Liye Wang, Nanjing (CN); Ke Xu, Nanjing (CN); Yuexin Yu, Nanjing (CN); Hongqiang Ren, Nanjing (CN)

(73) Assignee: Nanjing University, Nanjing (CN)

( * ) Notice: Subject to any disclaimer, the term of this patent is extended or adjusted under 35 U.S.C. 154(b) by 67 days.

(21) Appl. No.: 19/190,623

(22) Filed: Apr. 26, 2025

(65) Prior Publication Data

US 2025/0368946 A1 Dec. 4, 2025

(30) Foreign Application Priority Data

Jun. 4, 2024 (CN) .......................... 202410711288.7

(51) Int. Cl.
*C12N 1/12* (2006.01)

(52) U.S. Cl.
CPC ..................................... *C12N 1/12* (2013.01)

(58) Field of Classification Search
CPC ......................................................... C12N 1/12
See application file for complete search history.

(56) References Cited

U.S. PATENT DOCUMENTS

2011/0217764 A1 9/2011 Christenson et al.

FOREIGN PATENT DOCUMENTS

| CN | 102943028 A | 2/2013 |
| CN | 108163972 A | 6/2018 |
| CN | 112662564 B | 4/2022 |
| CN | 217127412 U | 8/2022 |
| CN | 116121058 A | 5/2023 |
| CN | 116296678 A | 6/2023 |

(Continued)

OTHER PUBLICATIONS

Christenson et al., "Rotating algal film bioreactor and spool harvester for waste water treatment with biofuels by-products," Biotechnology and Bioengineering 109(7):1674-1684, 2012.*

(Continued)

*Primary Examiner* — Rosanne Kosson
(74) *Attorney, Agent, or Firm* — Zhu Lehnhoff LLP

(57) ABSTRACT

An algal biofilm harvesting method capable of reducing release of planktonic microalgae includes the following steps: S1: constructing an algal biofilm treatment system; S2: calculating a cutting area; S3: harvesting microalgae biomass; and S4: cyclic harvesting. By constructing an algal biofilm treatment system, a surface of an algal biofilm can be regularly cut to harvest microalgae biomass, thereby keeping activity of the biofilm in a best state all the time. In addition, the harvested microalgae biomass can be used as a high-quality substrate for subsequent fermentation, which can achieve resource saving. Quality attainment of effluent from a sewage tank with planktonic microalgae as a suspended solid indicator can be achieved, the treated effluent can be prevented from deteriorating due to an increase of the planktonic microalgae, and a risk that the planktonic microalgae in the effluent of the algal biofilm affects a subsequent treatment process is reduced.

7 Claims, 7 Drawing Sheets

| 2 | 17 | 4 | 19 | 5 | 20 | 7 | 22 | 8 | 23 |
| 25 | 10 | 26 | 11 | 28 | 13 | 29 | 14 | 30 | 15 |
| 2 | 17 | 3 | 18 | 5 | 20 | 7 | 22 | 8 | 23 |
| 25 | 10 | 26 | 11 | 27 | 12 | 29 | 14 | 30 | 15 |
| 2 | 17 | 3 | 18 | 5 | 20 | 6 | 21 | 8 | 23 |
| 24 | 9 | 26 | 11 | 27 | 12 | 29 | 14 | 30 | 15 |
| 1 | 16 | 3 | 18 | 5 | 20 | 6 | 21 | 8 | 23 |
| 24 | 9 | 26 | 11 | 27 | 12 | 28 | 13 | 30 | 15 |
| 1 | 16 | 3 | 18 | 4 | 19 | 6 | 21 | 8 | 23 |
| 24 | 9 | 25 | 10 | 27 | 12 | 28 | 13 | 30 | 15 |
| 1 | 16 | 3 | 18 | 4 | 19 | 6 | 21 | 7 | 22 |
| 24 | 9 | 25 | 10 | 27 | 12 | 28 | 13 | 29 | 14 |
| 1 | 16 | 2 | 17 | 4 | 19 | 6 | 21 | 7 | 22 |
| 24 | 9 | 25 | 10 | 26 | 11 | 28 | 13 | 29 | 14 |
| 1 | 16 | 2 | 17 | 4 | 19 | 5 | 20 | 7 | 22 |

15 cm 10 cm

(56)         References Cited

FOREIGN PATENT DOCUMENTS

CN          117228801  A      12/2023
CN          117626889  A       3/2024

OTHER PUBLICATIONS

Notice of Grant of Patent Rights, issued in CN202410711288.7
(priority application), by CNIPA, dated Sep. 11, 2024.
Search Report, prepared by Beijing Zhanqiao Intellectual Property
Agency, dated Jun. 4, 2024.

* cited by examiner

| 2 | 17 | 4 | 19 | 5 | 20 | 7 | 22 | 8 | 23 |
|---|----|---|----|---|----|---|----|---|----|
| 25 | 10 | 26 | 11 | 28 | 13 | 29 | 14 | 30 | 15 |
| 2 | 17 | 3 | 18 | 5 | 20 | 7 | 22 | 8 | 23 |
| 25 | 10 | 26 | 11 | 27 | 12 | 29 | 14 | 30 | 15 |
| 2 | 17 | 3 | 18 | 5 | 20 | 6 | 21 | 8 | 23 |
| 24 | 9 | 26 | 11 | 27 | 12 | 29 | 14 | 30 | 15 |
| 1 | 16 | 3 | 18 | 5 | 20 | 6 | 21 | 8 | 23 |
| 24 | 9 | 26 | 11 | 27 | 12 | 28 | 13 | 30 | 15 |
| 1 | 16 | 3 | 18 | 4 | 19 | 6 | 21 | 8 | 23 |
| 24 | 9 | 25 | 10 | 27 | 12 | 28 | 13 | 30 | 15 |
| 1 | 16 | 3 | 18 | 4 | 19 | 6 | 21 | 7 | 22 |
| 24 | 9 | 25 | 10 | 27 | 12 | 28 | 13 | 29 | 14 |
| 1 | 16 | 2 | 17 | 4 | 19 | 6 | 21 | 7 | 22 |
| 24 | 9 | 25 | 10 | 26 | 11 | 28 | 13 | 29 | 14 |
| 1 | 16 | 2 | 17 | 4 | 19 | 5 | 20 | 7 | 22 |

ALGAL BIOFILM HARVESTING METHOD CAPABLE OF REDUCING RELEASE OF PLANKTONIC MICROALGAE

The present application claims the priority of Chinese patent application No. 202410711288.7, filed on 2024 Jun. 4, the entire disclose of which is incorporated herein by reference.

TECHNICAL FIELD

The present disclosure relates to the technical field of sewage treatment, and in particular to an algal biofilm harvesting method capable of reducing release of planktonic microalgae.

BACKGROUND

As the severity of global climate change becomes increasingly prominent, it has become a global consensus to achieve carbon neutrality. Sewage treatment, as an energy-intensive industry, is facing the challenge of technological innovation, and there is an urgent need to develop a low-carbon sewage treatment technology that can effectively remove pollutants in water and reduce greenhouse gas emissions at the same time. In recent years, the technology integrating microalgae cultivation with sewage treatment has attracted widespread attention. This technology not only can effectively remove nutrients such as nitrogen and phosphorus from the sewage, but also can enhance carbon fixation and storage through algal growth, thereby achieving synergistic effects in both pollution reduction and carbon mitigation. Compared with a suspension culture system, the algal biofilm wastewater treatment technology with biofilm culture as the core has remarkable advantages in biological load and biomass harvesting convenience, which is considered as one of the most potential alternative technologies to replace the existing secondary sewage treatment process and has broad application prospects.

Algal biofilm refers to the sessile growth communities mainly composed of microalgae growing on wet and light-receiving surfaces. The algal biofilm technology utilizes photosynthesis of the microalgae and its synergistic metabolism with bacteria (in algal-bacterial symbiosis) to transform pollutants in the sewage into biomass, while simultaneously absorbing carbon dioxide and releasing oxygen. To maintain the activity of biofilm in the best state and harvest biomass as a high-quality substrate for subsequent fermentation, it is necessary to harvest the biomass of algal biofilm regularly.

However, improper algal biofilm harvesting method will lead to the release of large quantities of planktonic microalgae into the water during the recovery process of the algal biofilm, which brings great challenges to the subsequent treatment process. In CN117228801, an algae collection device based on a magnetic coagulation process is provided, which includes a water intake tank, a coagulation tank and a separation tank arranged on a floating plate. The planktonic microalgae in the water forms magnetic flocs with magnetic seeds in the coagulation tank, and the separation assembly can separate the water, the algae and the magnetic seeds to achieve the separation and collection of the planktonic microalgae. In CN117626889A, a device for automatically removing planktonic microalgae in river courses is provided. By providing an overflow weir to form a water level difference in the river courses, a water inlet pipe is provided under a high water level of the overflow weir, so that the water inlet pipe can collect the water and planktonic microalgae near the high water level, thereby achieving the purpose of filtering and collecting the planktonic microalgae in the river.

However, all the foregoing prior art adopts an 'end-of-pipe treatment' approach, which applies planktonic microalgae capture techniques to scenarios where large quantities of planktonic microalgae have already proliferated. These methods have not optimized the algal biofilm harvesting method, and failed to solve the problems that improper harvesting methods lead to the release of planktonic microalgae from the source, and adding additional treatment steps leads to an increase in the overall cost.

SUMMARY

To solve the problem described above, the present disclosure provides an algal biofilm harvesting method capable of reducing release of planktonic microalgae, including the following steps:

S1: constructing an algal biofilm treatment system: placing a biofilm as a growth carrier of microalgae in a sewage tank, inoculating microalgae communities on the biofilm to form an algal biofilm, constructing an algal biofilm treatment system after maturation of the algal biofilm, and arranging a plurality of the algal biofilm treatment systems in the sewage tank in turn;

S2: calculating a cutting area: calculating a coverage area $T_A$ of a single algal biofilm, and dividing the algal biofilm into a plurality of cutting units with an area of $T_C$, wherein a total number of cuts is that $n = T_A/T_C$, setting the number of days $\Delta t$ required for cutting all cutting units of the single algal biofilm as a harvest cycle, wherein the number of cutting units cut per day is that $n_d = T_A/(\Delta t \times T_C) = n/\Delta t$;

S3: harvesting microalgae biomass: harvesting microalgae biomass from the single algal biofilm according to the area $T_C$ of the cutting unit and the number $n_d$ of cutting units cut per day, harvesting one cutting unit from a top corner of the algal biofilm, wherein in each harvest cycle, the cutting units on a same day have no adjacent sides, and the cutting units on adjacent days have no adjacent sides; and controlling a harvest cycle length between the cutting units with adjacent sides to be maximized; and S4: cyclic harvesting: after harvesting microalgae biomass in step S3 is completed once, harvesting the microalgae biomass again in a same method as in step S3 to achieve cyclic harvesting.

Further, the biofilm is made of a silicone film.

It should be noted that the biofilm made of the silicone film can be used as a good carrier for the growth and cultivation of the microalgae.

Further, a result obtained by dividing a length of the algal biofilm by a length of the cutting unit is an integer, and a result obtained by dividing a width of the algal biofilm by a width of the cutting unit is an integer, and the total number n of cuts is greater than or equal to 60 and less than or equal to 375.

It should be noted that the cutting steps can be implemented more conveniently by optimizing and adjusting a relationship between a length and width of the algal biofilm and a length and width of the cutting unit, the greater the cutting unit, the smaller to the total number n of cuts, and the more the quantity of planktonic microalgae released from the algal biofilm in a reconstruction process, with a possible reason that the center of the cutting unit with a large area is far from an edge, and the species with stronger planktonic ability in surrounding communities are more likely to occupy the surface of the cutting unit, which results in massive proliferation of planktonic microalgae. In addition, further reducing the cutting unit will have a marginal effect on reducing the gain of the release of the planktonic microalgae, and excessively small cutting unit may lead to overly cumbersome harvesting procedure. Therefore, it is necessary to control the size of the cutting unit within a reasonable range.

Further, a length-width ratio of the algal biofilm is 3:2 or 5:3.

It should be noted that by optimizing and adjusting the length-width ratio of the algal biofilm, the treatment effect of the algal biofilm on the sewage can be improved, and the microalgae biomass can be conveniently cut and harvested.

Further, the number $n_d$ of cutting units cut per day in step S2 is an integer, and the harvest cycle $\Delta t$ is greater than or equal to 7 d and less than or equal to 60 d.

It should be noted that by optimizing and adjusting the number $n_d$ of cutting units cut per day as an integer and optimizing an interval range of the harvest cycle $\Delta t$, it is convenient for staff to make statistics. The longer the harvest cycle, the less the quantity of the planktonic microalgae released. However, the release of the planktonic microalgae cannot be effectively controlled in a short harvest cycle, and therefore, the size of the scraped algal biofilm should be controlled synchronously with the harvest cycle of the biomass.

Furthermore, in step S3, a specific harvesting method of the microalgae biomass is as follows:

S3-1: harvesting one cutting unit from a top corner of the algal biofilm, after collecting one cutting unit along a long side of the algal biofilm, collecting a next cutting unit at an interval of one cutting unit, and harvesting the microalgae biomass from the algal biofilm in sequence until the number of cuts reaches the number of cutting units cut per day;

S3-2: next day, continuing to collect a next cutting unit along a same direction by a cutting method in step S3-1 from a position spaced apart from a previous cutting unit by one cutting unit, if a cutting path has reached a maximum allowable travel distance along the long side of the algal biofilm in the middle, continuously to start traveling again along the long side of the algal biofilm from a position flush with an initial cutting unit at the top corner at an interval of a width of one cutting unit;

S3-3: when a displacement of a column interval of the cutting unit along a short side of the algal biofilm reaches a maximum movable value, starting from an inner vertex of the initial cutting unit at the top corner of the algal biofilm, continuing to harvest the algal biofilm along the long side of the algal biofilm by the cutting method in step S3-1 from a position after respectively moving a length and a width of one cutting unit along the short and long sides of the algal biofilm, when the cutting path reaches the bottom along the long side of the algal biofilm, continuing to travel along the long side from a position flush with the initial cutting unit in the step at an interval of the width of one cutting unit;

S3-4: when a displacement of a column interval of the cutting unit along the short side of the algal biofilm reaches a maximum movable value in step S3-3, starting from the initial cutting unit at the top corner, continuing to harvest the algal biofilm along the long side of the algal biofilm by the cutting method in Step S3-1 from a position of the cutting unit intersecting the short side and a side edge of the algal biofilm, and when the cutting path reaches the bottom along the long side of the algal biofilm, continuing to travel along the long side from a position flush with the initial cutting unit in the step at an interval of the width of one cutting unit;

S3-5: when a displacement of a column interval of the cutting unit along the short side of the algal biofilm reaches a maximum movable value in step S3-4, starting from the initial cutting unit at the top corner, continuing to harvest the algal biofilm along the long side of the algal biofilm by the cutting method in Step S3-1 from a position of the cutting unit intersecting the long side and the side edge of the algal biofilm, and when the cutting path reaches the bottom along the long side of the algal biofilm, continuing to travel along the long side from a position flush with the initial cutting unit in the step at an interval of the width of one cutting unit;

S3-6: when a displacement of a column interval of the cutting unit along the short side of the algal biofilm reaches a maximum movable value in step S3-5, completing one harvest cycle $\Delta t$.

Preferably, in step S1, the biofilm as a growth carrier of microalgae is wound on upper and lower drive shafts in the form of a conveyor belt and rotates synchronously with the drive shafts, the lower drive shaft is immersed in the sewage tank, the biofilm is inoculated with microalgae communities to form the algal biofilm, and one algal biofilm treatment system is constructed after the algal biofilm matures. In step S3, two algal biofilms on both sides of the single algal biofilm treatment system are taken as two independent algal biofilms and are respectively used for harvesting microalgae biomass. For the algal biofilm at one side, when harvesting the microalgae biomass, the rotating drive shaft is stopped to a fixed position for microalgae biomass collection, and one cutting unit is harvested from a top corner of the algal biofilm, the drive shaft is continuously started to rotate the algal biofilm treatment system after harvesting is completed, and the microalgae biomass is synchronously harvested by the algal biofilms on both sides in a mirror-image symmetrical manner.

It should be noted that the algal biofilm is driven by the conveyor belt to rotate continuously, which can improve the sewage treatment efficiency and facilitate the cutting and harvesting. By synchronizing the algal biofilms on both sides in a mirror-image symmetrical manner, it is ensured that the algal biofilms always maintain good treatment efficiency for sewage during cutting and harvesting.

Preferably, each algal biofilm treatment system in the sewage tank is configured to harvest the microalgae biomass independently and synchronously according to steps in S3-1 to S3-5.

Further, in step S3, the microalgae biomass is harvested by a scraper or hydraulic cutting.

Compared with the prior art, the present disclosure has beneficial effects as follows:

By constructing an algal biofilm treatment system, a surface of an algal biofilm can be regularly cut to harvest microalgae biomass, thereby keeping activity of the biofilm in a best state all the time. In addition, the harvested microalgae biomass can be used as a high-quality substrate for subsequent fermentation, which can achieve resource saving. In specific cutting and harvesting steps, synchronous limitation of the size of the scraped algal biofilm and the harvest cycle of harvesting the microalgae biomass can inhibit the quantity of planktonic microalgae released from the algal biofilm in the process of remodeling the biofilm.

Quality attainment of effluent from a sewage tank with planktonic microalgae as a suspended solid indicator can be achieved without setting subsequent steps for removing the planktonic microalgae, the treated effluent can be prevented from deteriorating due to an increase of the planktonic microalgae, and a risk that the planktonic microalgae in the effluent of the algal biofilm affects a subsequent treatment process is reduced.

By optimizing and adjusting the number $n_d$ of cutting units cut per day as an integer and synchronously optimizing an interval range of the harvest cycle $\Delta t$, it is convenient for staff to make statistics, which can effectively control the release of the planktonic microalgae.

By optimizing and adjusting the total number of cuts, the size of the cutting unit can be controlled in a reasonable range, which can effectively control the release of the planktonic microalgae.

BRIEF DESCRIPTION OF THE DRAWINGS

FIG. 2 is a diagram of a harvesting procedure of microalgae biomass according to Embodiment 1 of the present disclosure;

Figure 1:
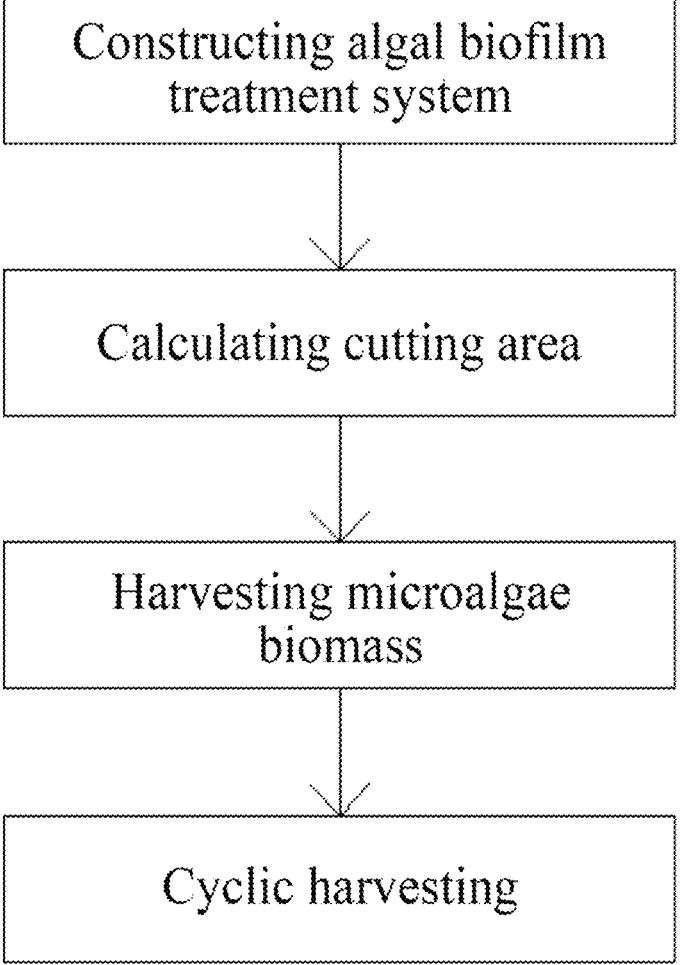
FIG. 1 is a flow chart of a method according to the present disclosure.

In the drawings: 1-biofilm; 2-drive shaft.

DETAILED DESCRIPTION OF THE EMBODIMENTS

To further illustrate adopted ways and obtained effects of the present disclosure, the technical solution of the present disclosure will be described clearly and completely below with experiments.

Embodiment 1: An algal biofilm harvesting method capable of reducing release of planktonic microalgae in this embodiment includes the following steps:

S1: construction of an algal biofilm treatment system: a biofilm 1 as a growth carrier of microalgae is placed in a sewage tank, microalgae communities are inoculated on the biofilm 1 to form an algal biofilm, an algal biofilm treatment system is constructed after the algal biofilm matures, and multiple the algal biofilm treatment systems are arranged in the sewage tank in turn;

S2: calculation of a cutting area: a coverage area $T_A$ of a single algal biofilm is calculated, the algal biofilm is divided into multiple cutting units which have an area of $T_C$, and a total number of cuts is that $n=T_A/T_C$, the number of days $\Delta t$ required for cutting all cutting units of the single algal biofilm is set as a harvest cycle, where the number of cutting units cut per day is that $n_d=T_A/(\Delta t \times T_C)=n/\Delta t$, a result obtained by dividing a length of the algal biofilm by a length of the cutting unit is an integer, a result obtained by dividing a width of the algal biofilm by a width of the cutting is an integer, and a total number n of cuts is 150; a length-width ratio of the algal biofilm is 3:2, the number $n_d$ of cutting units cut per day is an integer, and the harvest cycle $\Delta t$ is 30 d;

S3: harvesting of microalgae biomass: microalgae biomass is harvested from the single algal biofilm according to the area $T_C$ of the cutting unit and the number $n_d$ of cutting units cut per day, one cutting unit is harvested from a top corner of the algal biofilm, where in each harvest cycle, the cutting units on a same day have no adjacent sides, and the cutting units on adjacent days have no adjacent sides; and a harvest cycle length between the cutting units with adjacent sides is controlled to be maximized;

A specific harvesting method of the microalgae biomass is as follows:

S3-1: one cutting unit is harvested from a top corner of the algal biofilm, after collecting one cutting unit along a long side of the algal biofilm, a next cutting unit is collected at an interval of one cutting unit, and the microalgae biomass is harvested from the algal biofilm in sequence until the number of cuts reaches the number $n_d$ of cutting units cut per day;

S3-2: next day, a next cutting unit is continuously collected along a same direction by a cutting method in step S3-1 from a position spaced apart from a previous cutting unit by one cutting unit, if a cutting path has reached a maximum allowable travel distance along the long side of the algal biofilm in the middle, traveling is continuously started again along the long side of the algal biofilm from a position flush with an initial cutting unit at the top corner at an interval of a width of one cutting unit;

S3-3: when a displacement of a column interval of the cutting unit along a short side of the algal biofilm reaches a maximum movable value, starting from an inner vertex of the initial cutting unit at the top corner of the algal biofilm, the algal biofilm is continuously harvested along the long side of the algal biofilm by the cutting method in step S3-1 from a position after respectively moving a length and a width of one cutting unit along the short and long sides of the algal biofilm, when the cutting path reaches the bottom along the long side of the algal biofilm, traveling is continuously started again along the long side from a position flush with the initial cutting unit in the step at an interval of the width of one cutting unit;

S3-4: when a displacement of a column interval of the cutting unit along the short side of the algal biofilm reaches a maximum movable value in step S3-3, starting from the initial cutting unit at the top corner, the algal biofilm is continuously harvested along the long side of the algal biofilm by the cutting method in Step S3-1 from a position of the cutting unit intersecting the short side and a side edge of the algal biofilm, and when the cutting path reaches the bottom along the long side of the algal biofilm, traveling is continuously started again along the long side from a position flush with the initial cutting unit in the step at an interval of the width of one cutting unit;

S3-5: when a displacement of a column interval of the cutting unit along the short side of the algal biofilm reaches a maximum movable value in step S3-4, starting from the initial cutting unit at the top corner, the algal biofilm is continuously harvested along the long side of the algal biofilm by the cutting method in Step S3-1 from a position of the cutting unit intersecting the long side and the side edge of the algal biofilm, and when the cutting path reaches the bottom along the long side of the algal biofilm, traveling is continuously started again along the long side from a position flush with the initial cutting unit in the step at an interval of the width of one cutting unit;

S3-6: when a displacement of a column interval of the cutting unit along the short side of the algal biofilm reaches a maximum movable value in step S3-5, one harvest cycle Δt is completed;

each algal biofilm treatment system in the sewage tank is configured to harvest the microalgae biomass independently and synchronously according to steps in S3-1 to S3-5, and the microalgae biomass is harvested with a scraper; and S4: cyclic harvesting: after harvesting microalgae biomass in step S3 is completed once, the microalgae biomass is harvested again in a same method as in step S3 to achieve cyclic harvesting.

Embodiment: 2: an algal biofilm harvesting method capable of reducing release of planktonic microalgae in this embodiment includes the following steps:

S1: construction of an algal biofilm treatment system: a biofilm 1 made of a silicone film and serving as a microalgae growth carrier is wound on an upper drive shaft 2 and a lower drive shaft 2 in the form of a conveyor belt and rotates synchronously with the drive shafts 2, a lower drive shaft 2 is immersed in a sewage tank, microalgae communities are inoculated on the biofilm 1 to form an algal biofilm, an algal biofilm treatment system is constructed after the algal biofilm matures, and multiple the algal biofilm treatment systems are arranged in the sewage tank in turn;

S2: calculation of a cutting area: a coverage area $T_A$ of a single algal biofilm is calculated, the algal biofilm is divided into multiple cutting units which have an area of $T_C$, and a total number of cuts is that $n=T_A/T_C$, the number of days Δt required for cutting all cutting units of the single algal biofilm is set as a harvest cycle, where the number of cutting units cut per day is that $n_d=T_A/(Δt×T_C)=n/Δt$, a result obtained by dividing a length of the algal biofilm by a length of the cutting unit is an integer, a result obtained by dividing a width of the algal biofilm by a width of the cutting is an integer, and a total number n of cuts is 150; a length-width ratio of the algal biofilm is 5:3, the number $n_d$ of cutting units cut per day is an integer, and the harvest cycle Δt is 30 d;

S3: harvesting of microalgae biomass: microalgae biomass can be simultaneously harvested from the algae biofilms on both sides of a single algae biofilm treatment system according to the area $T_C$ of the cutting unit and the number $n_d$ of cutting units cut per day, the algal biofilms on both sides of the single algal biofilm treatment system are taken as two independent algal biofilms and are respectively used for harvesting microalgae biomass; for the algal biofilm at one side, when harvesting the microalgae biomass, the rotating drive shaft 2 is stopped to a fixed position for microalgae biomass collection, and one cutting unit is harvested from a top corner of the algal biofilm, the drive shaft 2 is continuously started to rotate the algal biofilm treatment system after harvesting is completed, and the microalgae biomass is synchronously harvested by the algal biofilms on both sides in a mirror-image symmetrical manner; in each harvest cycle, the cutting units on a same day have no adjacent sides, and the cutting units on adjacent days have no adjacent sides; and a harvest cycle length between the cutting units with adjacent sides is controlled to be maximized;

for the algal biofilm on one side, a specific harvesting method of the microalgae biomass is as follows:

S3-1: one cutting unit is harvested from a top corner of the algal biofilm, after collecting one cutting unit along a long side of the algal biofilm, a next cutting unit is collected at an interval of one cutting unit, and the microalgae biomass is harvested from the algal biofilm in sequence until the number of cuts reaches the number $n_d$ of cutting units cut per day;

S3-2: next day, a next cutting unit is continuously collected along a same direction by a cutting method in step S3-1 from a position spaced apart from a previous cutting unit by one cutting unit, if a cutting path has reached a maximum allowable travel distance along the long side of the algal biofilm in the middle, traveling is continuously started again along the long side of the algal biofilm from a position flush with an initial cutting unit at the top corner at an interval of a width of one cutting unit;

S3-3: when a displacement of a column interval of the cutting unit along a short side of the algal biofilm reaches a maximum movable value, starting from an inner vertex of the initial cutting unit at the top corner of the algal biofilm, the algal biofilm is continuously harvested along the long side of the algal biofilm by the cutting method in step S3-1 from a position after respectively moving a length and a width of one cutting unit along the short and long sides of the algal biofilm, when the cutting path reaches the bottom along the long side of the algal biofilm, traveling is continuously started again along the long side from a position flush with the initial cutting unit in the step at an interval of the width of one cutting unit;

S3-4: when a displacement of a column interval of the cutting unit along the short side of the algal biofilm reaches a maximum movable value in step S3-3, starting from the initial cutting unit at the top corner, the algal biofilm is continuously harvested along the long side of the algal biofilm by the cutting method in Step S3-1 from a position of the cutting unit intersecting the short side and a side edge of the algal biofilm, and when the cutting path reaches the bottom along the long side of the algal biofilm, traveling is continuously started again along the long side from a position flush with the initial cutting unit in the step at an interval of the width of one cutting unit;

S3-5: when a displacement of a column interval of the cutting unit along the short side of the algal biofilm reaches a maximum movable value in step S3-4, starting from the initial cutting unit at the top corner, the algal biofilm is continuously harvested along the long side of the algal biofilm by the cutting method in Step S3-1 from a position of the cutting unit intersecting the long side and the side edge of the algal biofilm, and when the cutting path reaches the bottom along the long side of the algal biofilm, traveling is continuously started again along the long side from a position flush with the initial cutting unit in the step at an interval of the width of one cutting unit;

S3-6: when a displacement of a column interval of the cutting unit along the short side of the algal biofilm reaches a maximum movable value in step S3-5, one harvest cycle Δt is completed;

the simultaneous harvesting of the microalgae biomass from the microalgal biofilms on both sides of the single algal biofilm treatment system is synchronously carried out in a mirror-image symmetrical manner, each microalgal biofilm treatment system in the sewage tank is configured to harvest microalgae biomass independently and synchronously according to the steps in S3-1 to S3-5, and the microalgae biomass is harvested by hydraulic cutting; and S4: cyclic harvesting: after harvesting microalgae biomass in step S3 is completed once, the microalgae biomass is harvested again in a same method as in step S3 to achieve cyclic harvesting.

Embodiment 3: a difference between this embodiment and Embodiment 2 is that the total number n of cuts is 1500.

Embodiment 4: a difference between this embodiment and Embodiment 2 is that the total number n of cuts is 375.

Embodiment 5: a difference between this embodiment and Embodiment 2 is that the total number n of cuts is 75.

Embodiment 6: a difference between this embodiment and Embodiment 2 is that the total number n of cuts is 60.

Embodiment 7: a difference between this embodiment and Embodiment 2 is that the harvest cycle Δt is 7 d.

Embodiment 8: a difference between this embodiment and Embodiment 2 is that the harvest cycle Δt is 14 d.

Embodiment 9: a difference between this embodiment and Embodiment 2 is that the harvest cycle Δt is 60 d.

Embodiment 10: a difference between this embodiment and Embodiment 2 is that a length-width ratio of the algal biofilm is 3:2, and a physical harvesting way by cutting is hydraulic cutting.

Experimental Example 1: To clarify the feasibility of an algal biofilm harvesting method capable of reducing release of planktonic microalgae, the parameters in Embodiment 2 are used as an example to carry out an experiment. A size of the single algal biofilm is 15 cm (length)×10 cm (width), an illumination intensity is set at 130 μmol/s·m², an illumination duration is 12 h/d, hydraulic retention time is 24 h, and an influent is simulated municipal sewage (with chemical oxygen demand concentration of 180 mg/L, an ammonia nitrogen concentration of 40 mg/L, a total phosphorous concentration of 3.5 mg/L, and a proper amount of other trace elements). After the algal biofilm matures, an algal biofilm harvesting procedure is developed according to steps in Embodiment 10:

In step S2, a coverage area $T_A$ of the single algal biofilm is calculated to be equal to 150 cm².

When harvesting microalgae biomass in step S3, a rotating drive shaft 2 is stopped to a fixed position for microalgae biomass collection, a harvesting method of gouging with a stainless-steel scraper is adopted, it is set that the area $T_C$ of the cutting unit is 1 cm², the total number n of cuts is 150, the harvest cycle Δt is 30 d, and the number $n_d$ of cutting units cut per day is 5. After the harvesting is completed, the drive shaft 2 is continuously started to rotate the algal biofilm treatment system.

The biomass harvesting is carried out as shown in FIG. 2, each block is a cutting unit, and the number in the square represents the number of days required to harvest the cutting unit in one harvest cycle. In this experiment, the harvest cycle Δt is 30 d, so the number of days is 1 to 30. The specific procedures are described as steps S3-1~S3-5. Taking a situation on a ninth day as an example, when a displacement of a column interval of the cutting unit along a short side of the algal biofilm reaches a maximum movable value, starting from an inner vertex of the initial cutting unit at the top corner of the algal biofilm, the algal biofilm is continuously harvested along the long side of the algal biofilm in a manner of "collecting a next cutting unit at an interval of one cutting unit after harvesting one cutting unit" from a position after respectively moving a length and a width of one cutting unit along the short and long sides of the algal biofilm. Taking a situation on a tenth day as an example, when the cutting path reaches the bottom along the long side, traveling is continuously started again along the long side from a position flush with an initial cutting unit in step S3-3 at an interval of a width of one cutting unit. Taking a situation on a sixteenth day as an example, when the displacement of a column interval of the cutting unit along a short side of the algal biofilm reaches a maximum movable value, the algal biofilm is continuously harvested along the long side of the algal biofilm in a manner of "collecting a next cutting unit at an interval of one cutting unit after harvesting one cutting unit" from a position of the cutting unit intersecting the short side and a side edge of the algal biofilm. Taking a situation on a seventeenth day as an example, when the cutting path reaches the bottom along the long side, traveling is continuously started again along the long side from a position flush with an initial cutting unit in step S3-4 at an interval of a width of one cutting unit. Taking a situation on a twenty-fourth day as an example, when the displacement of a column interval of the cutting unit along a short side of the algal biofilm reaches a maximum movable value, the algal biofilm is continuously harvested along the long side of the algal biofilm in a manner of "collecting a next cutting unit at an interval of one cutting unit after harvesting one cutting unit" from a position of the cutting unit intersecting the long side and the side edge of the algal biofilm. Taking a situation on a twenty-fifth day as an example, when the cutting path reaches the bottom along the long side, traveling is continuously started again along the long side from a position flush with an initial cutting unit in step S3-5 at an interval of a width of one cutting unit until one harvest cycle is completed.

The harvesting of the algal biofilm on the other side of the same algal biofilm treatment system is carried out synchronously in a mirror-image pattern relative to that in FIG. 2. After three harvest cycles, the concentrations of chemical oxygen demand, total nitrogen and total phosphorus in the water are determined by a potassium dichromate method and spectrophotometry, and a yield of the microalgae biomass and the content of volatile total suspended solids in the water are determined simultaneously by a gravimetric method.

In this embodiment, when the effluent of the algal biofilm treatment system is stably achieves the concentration of chemical oxygen demand of less than 30 mg/L, the concentration of total nitrogen of less than 5 mg/L and the concentration of total phosphorus of less than 0.3 mg/L, the release quantity of the planktonic microalgae (calculated by total volatile suspended solids (VSS)) is less than 5 mg/L.

Figure 3:
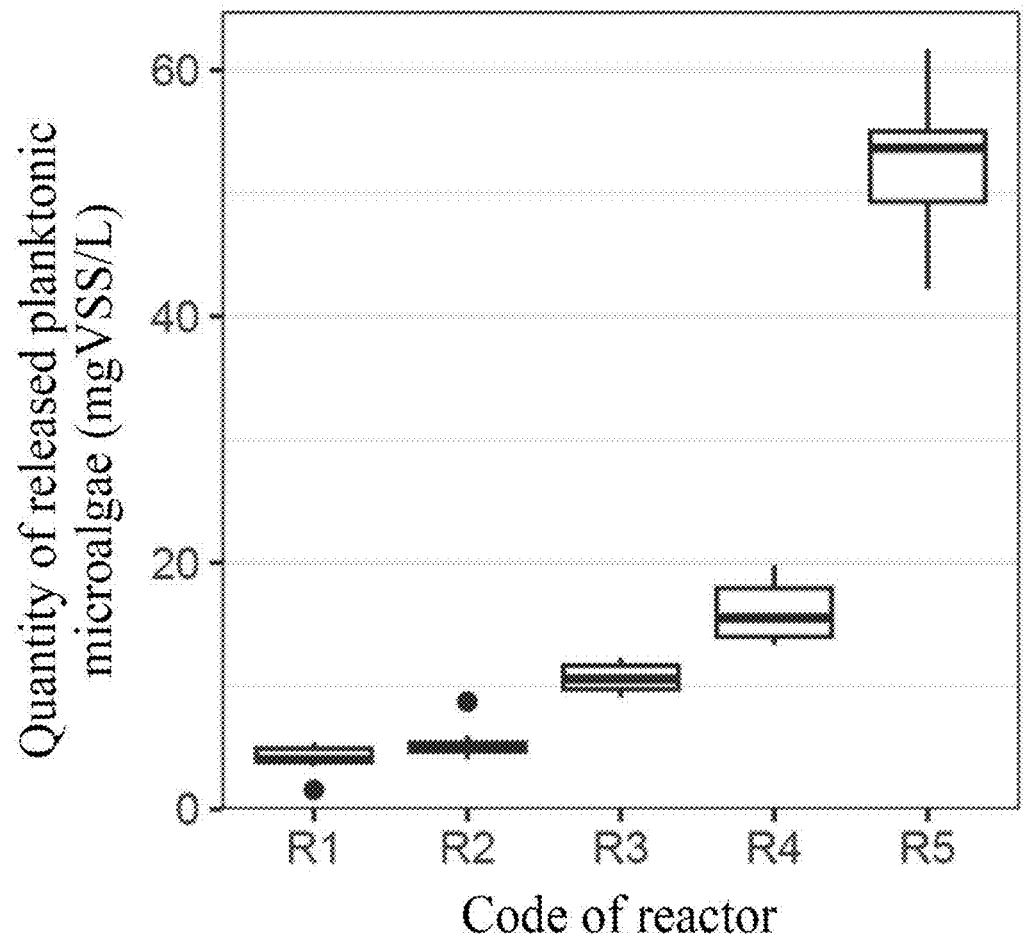
FIG. 3 is a diagram of release quantity of planktonic microalgae in effluent of each algal biofilm treatment system according to Embodiment 2 of the present disclosure.

Experimental Example 2: To verify the influence of the number of cutting units on the release quantity of the planktonic microalgae, experiments are carried out with the parameters in Embodiments 2-6, and five groups of algal biofilm treatment systems are provided, namely R1, R2, R3, R4 and R5. The size of a single algal biofilm is 25 cm (length)×15 cm (width), and areas of the cutting units are set so that R1 is 0.25 cm², R2 is 1 cm², R3 is 2.5 cm², R4 is 5 cm², and R5 is 6.25 cm², and the harvest cycle of each of five reactors is 30 d. The specific procedures are described as steps S3-1-S3-5 in Embodiment 1, and can be correspondingly adjusted according to the actual cutting area and the number of cutting units cut per day for scraping. The simulated sewage and operating conditions are consistent with those in Experimental Example 1. After three harvest cycles, the total volatile suspended solids (VSS) content in the water is determined by a gravimetric method to indicate the quantity of the released planktonic microalgae, with results shown in FIG. 3.

It can be known that the larger the cutting unit, the more the quantity of the planktonic microalgae released from the algal biofilm in the reconstruction process, with a possible reason that the center of the cutting unit with a large area is far from an edge, and the species with stronger planktonic ability in surrounding communities are more likely to occupy the surface of the cutting unit, which results in massive proliferation of planktonic microalgae. In addition, further reducing the cutting unit will have a marginal effect on reducing the gain of the release of the planktonic microalgae, and excessively small cutting unit may lead to overly cumbersome harvesting procedure. Therefore, it is necessary to control the size of the cutting unit within a reasonable range (60≤the total cutting number≤375).

Experimental Example 3: To verify the influence of the harvest cycle on the release quantity of the planktonic microalgae, parameters in Embodiment 2, Embodiment 7 to Embodiment 9 are used for carrying out an experiment, four groups of algal biofilm treatment systems are provided, and harvest cycles are respectively set as 7 d, 14 d, 30 d, and 60 d. The cutting unit is set as 1 cm², the specific procedure is as described in steps S3-1 to S3-5 in Embodiment 1, and is correspondingly adjusted according to the number of cutting units cut per day for developing the harvesting. The conditions such as simulated sewage and operating parameters are consistent with Experimental Example 1. After three harvest cycles, the content of volatile total suspended solids and the content of chlorophyll a in water are determined by a gravimetric method and spectrophotometry to indicate the quantity of planktonic microalgae released. In addition, the yield of the biomass of the algal biofilm is analyzed by the gravimetric method, with results shown in FIG. 4 to FIG. 6.

Figure 4:
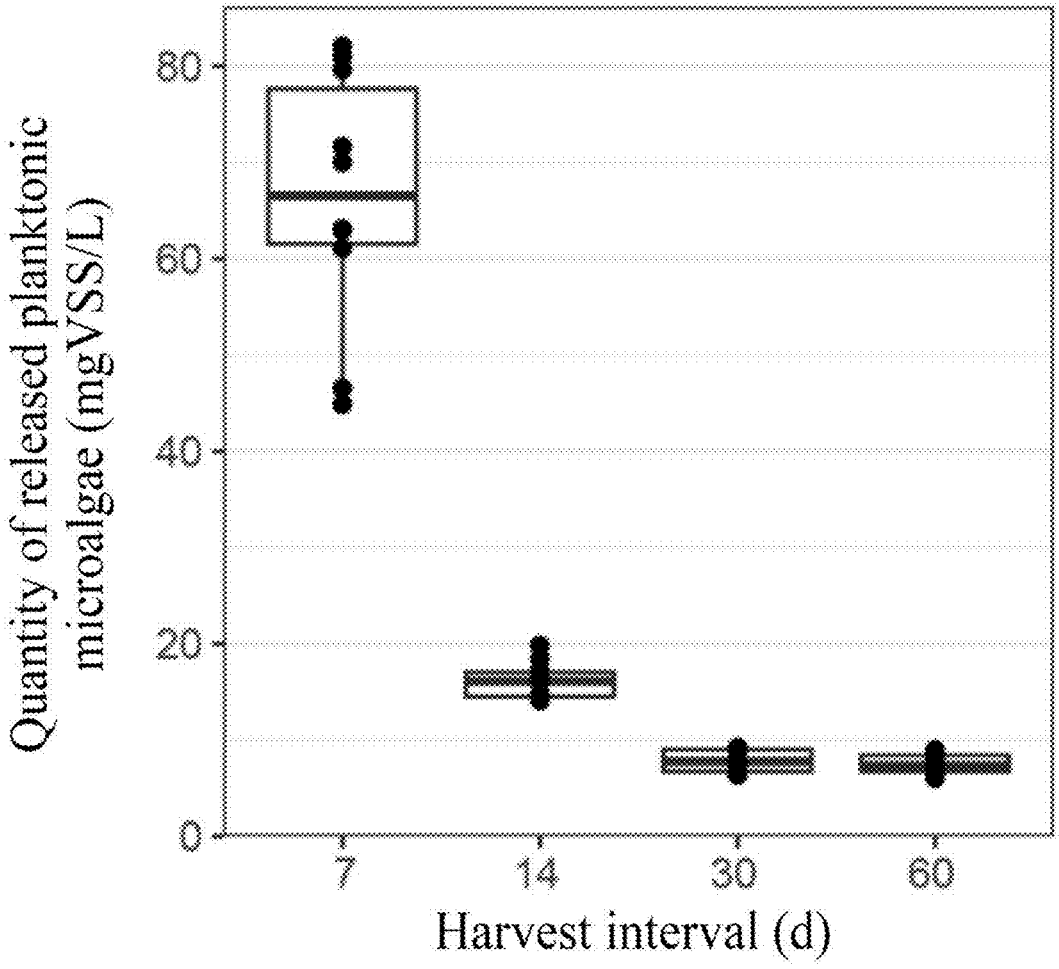
FIG. 4 is a diagram of a content of volatile total suspended solids in effluent of each algal biofilm treatment system according to Embodiment 3 of the present disclosure.
Figure 5:
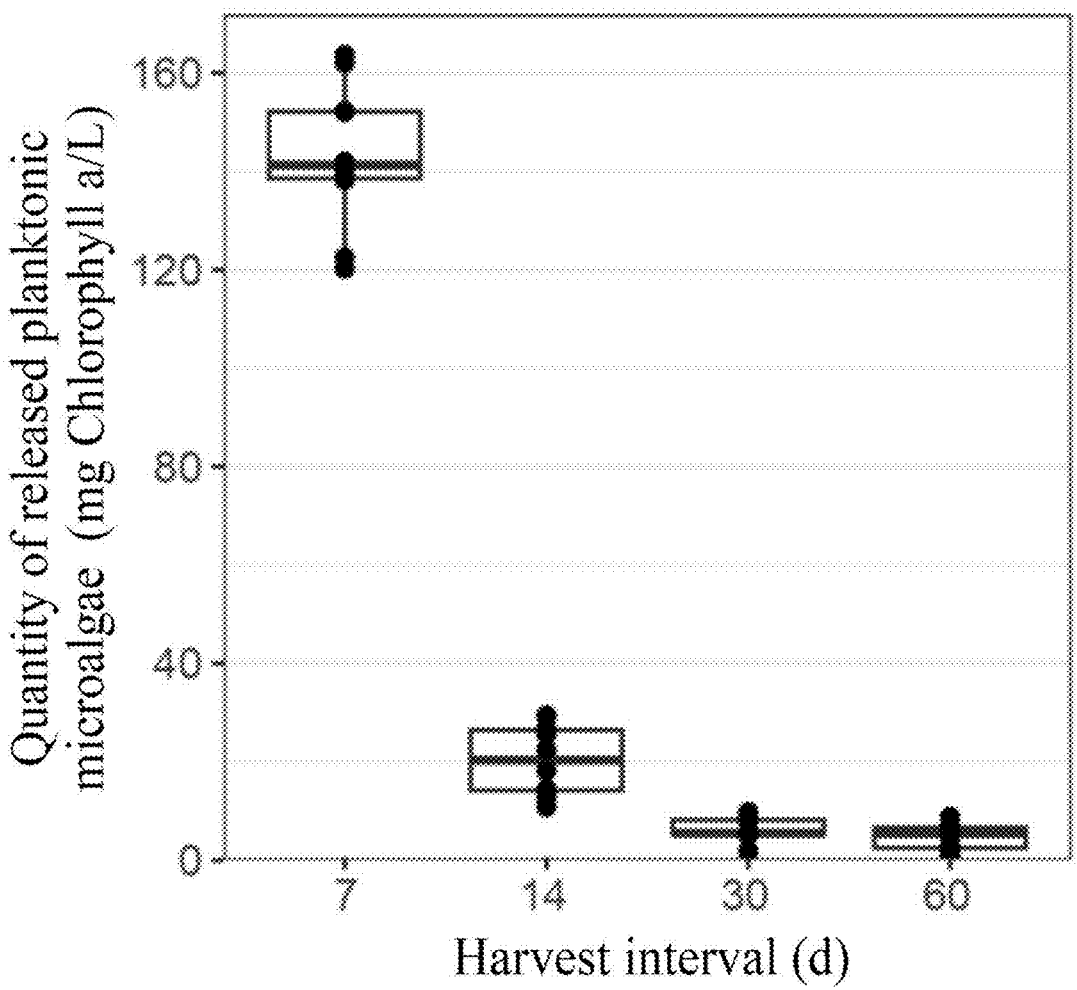
FIG. 5 is a diagram of a content of chlorophyll in effluent of each algal biofilm treatment system according to Embodiment 3 of the present disclosure.

Results in FIG. 4 and FIG. 5 show that the longer the harvest cycle, the less the quantity of the planktonic microalgae released. In addition, the results in FIG. 4 and FIG. 5 also indicate that the release of the planktonic microalgae cannot be effectively controlled in a short harvest cycle (7 d) if only the size of the cutting unit is controlled. Therefore, the size of the scraped algal biofilm and the harvest cycle time of the biomass need to be synchronously controlled.

Figure 6:
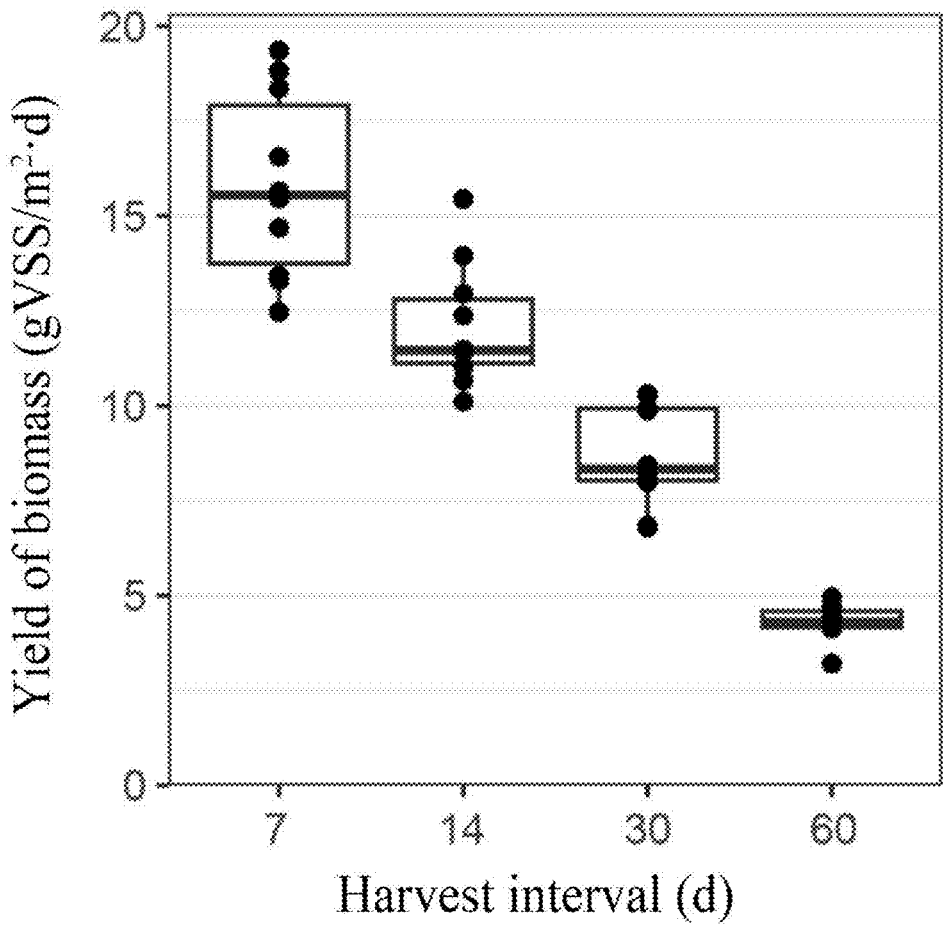
FIG. 6 is a diagram of a yield of biomass of an algal biofilm in each algal biofilm treatment system according to Embodiment 3 of the present disclosure.
Figure 7:
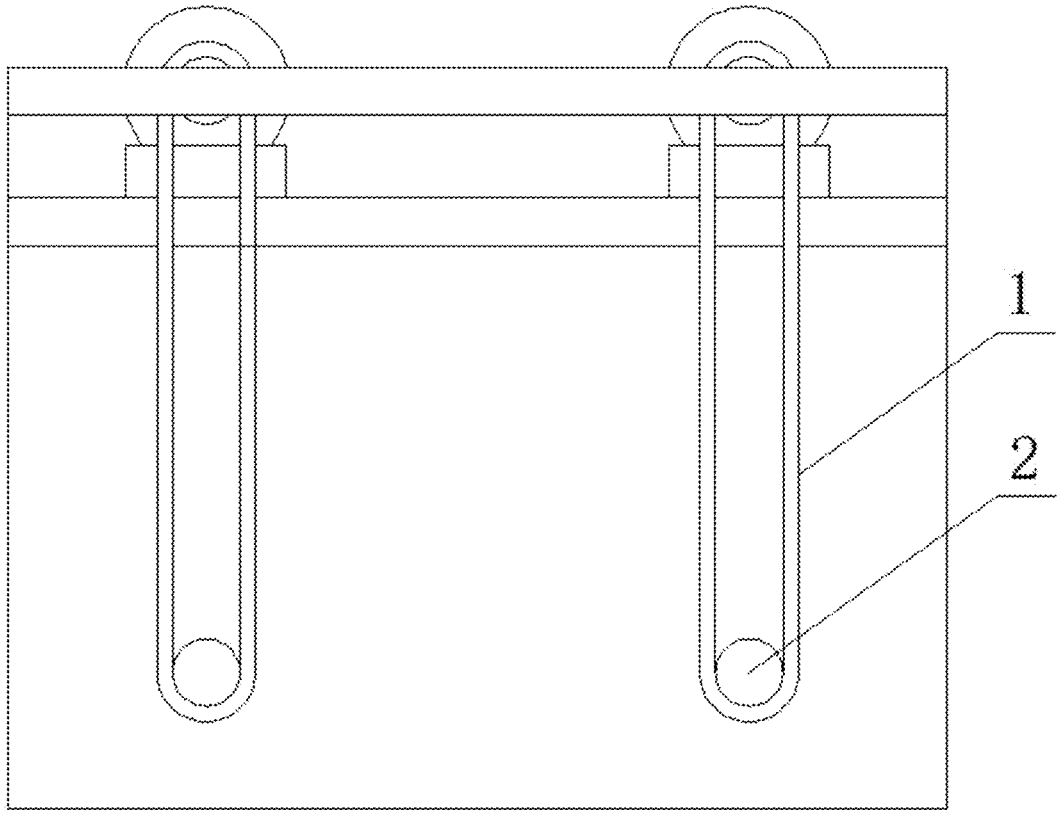
FIG. 7 is a diagram of an algal biofilm treatment system according to Embodiment 2 of the present disclosure.

The result in FIG. 6 indicates that excessively prolonging the harvest cycle (>30 days) will lead to the decrease of the yield of the microalgae biomass, but the yield of the biomass is directly related to the sewage treatment efficiency and carbon fixation efficiency of the algal biofilm. Therefore, controlling the harvest cycle within a reasonable range (14-30 d) can give consideration to pollution reduction and carbon reduction efficiency of the algal biofilm and the effect of inhibiting the release of the planktonic microalgae.

The invention claimed is:

1. An algal biofilm harvesting method capable of reducing release of planktonic microalgae, comprising the following steps:

S1: constructing an algal biofilm treatment system: placing a biofilm (1) as a growth carrier of microalgae in a sewage tank, inoculating microalgae communities on the biofilm (1) to form an algal biofilm, constructing an algal biofilm treatment system after maturation of the algal biofilm, and arranging a plurality of the algal biofilm treatment systems in the sewage tank in turn;

S2: calculating a cutting area: calculating a coverage area $T_A$ of a single algal biofilm, and dividing the algal biofilm into a plurality of cutting units with an area of $T_C$, wherein a total number of cuts is that $n=T_A/T_C$, setting the number of days $\Delta t$ required for cutting all cutting units of the single algal biofilm as a harvest cycle, wherein the number of cutting units cut per day is that $n_d=T_A/(\Delta t \times T_C)=n/\Delta t$;

S3: harvesting microalgae biomass: harvesting microalgae biomass from the single algal biofilm according to the area $T_C$ of the cutting unit and the number $n_d$ of cutting units cut per day, harvesting one cutting unit from a top corner of the algal biofilm, wherein in each harvest cycle, the cutting units on a same day have no adjacent sides, and the cutting units on adjacent days have no adjacent sides; and controlling a harvest cycle length between the cutting units with adjacent sides to be maximized;

wherein in step S3, a specific harvesting method of the microalgae biomass is as follows:

S3-1: harvesting one cutting unit from a top corner of the algal biofilm, after collecting one cutting unit along a long side of the algal biofilm, collecting a next cutting unit at an interval of one cutting unit, and harvesting the microalgae biomass from the algal biofilm in sequence until the number of cuts reaches the number of cutting units cut per day;

S3-2: next day, continuing to collect a next cutting unit along a same direction by a cutting method in step S3-1 from a position spaced apart from a previous cutting unit by one cutting unit, if a cutting path has reached a maximum allowable travel distance along the long side of the algal biofilm in the middle, continuing to start traveling again along the long side of the algal biofilm from a position flush with an initial cutting unit at the top corner at an interval of a width of one cutting unit;

S3-3: when a displacement of a column interval of the cutting unit along a short side of the algal biofilm reaches a maximum movable value, starting from an inner vertex of the initial cutting unit at the top corner of the algal biofilm, continuing to harvest the algal biofilm along the long side of the algal biofilm by the cutting method in step S3-1 from a position after respectively moving a length and a width of one cutting unit along the short and long sides of the algal biofilm, when the cutting path reaches the bottom along the long side of the algal biofilm, continuing to travel along the long side from a position flush with the initial cutting unit in the step at an interval of the width of one cutting unit;

S3-4: when a displacement of a column interval of the cutting unit along the short side of the algal biofilm reaches a maximum movable value in step S3-3, starting from the initial cutting unit at the top corner, continuing to harvest the algal biofilm along the long side of the algal biofilm by the cutting method in Step S3-1 from a position of the cutting unit intersecting the short side and a side edge of the algal biofilm, and when the cutting path reaches the bottom along the long side of the algal biofilm, continuing to travel along the long side from a position flush with the initial cutting unit in the step at an interval of the width of one cutting unit;

S3-5: when a displacement of a column interval of the cutting unit along the short side of the algal biofilm reaches a maximum movable value in step S3-4, starting from the initial cutting unit at the top corner, continuing to harvest the algal biofilm along the long side of the algal biofilm by the cutting method in Step S3-1 from a position of the cutting unit intersecting the long side and the side edge of the algal biofilm, and when the cutting path reaches the bottom along the long side of the algal biofilm, continuing to travel along the long side from a position flush with the initial cutting unit in the step at an interval of the width of one cutting unit;

S3-6: when a displacement of a column interval of the cutting unit along the short side of the algal biofilm reaches a maximum movable value in step S3-5, completing one harvest cycle $\Delta t$;

wherein in step S1, the biofilm (1) as a growth carrier of microalgae is wound on upper and lower drive shafts (2) in the form of a conveyor belt and rotates synchronously with the drive shafts (2), the lower drive shaft (2) is immersed in the sewage tank, the biofilm (1) is inoculated with microalgae communities to form the algal biofilm, and one algal biofilm treatment system is constructed after the algal biofilm matures; in step S3, two algal biofilms on both sides of the single algal biofilm treatment system are taken as two independent algal biofilms and are respectively used for harvesting microalgae biomass; for the algal biofilm at one side, when harvesting the microalgae biomass, the rotating drive shaft (2) is stopped to a fixed position for microalgae biomass collection, and one cutting unit is harvested from a top corner of the algal biofilm, the drive shaft (2) is continuously started to rotate the algal biofilm treatment system after harvesting is completed, and the microalgae biomass is synchronously harvested by the algal biofilms on both sides in a mirror-image symmetrical manner; and S4: cyclic harvesting: after harvesting microalgae biomass in step S3 is completed once, harvesting the microalgae biomass again in a same method as in step S3 to achieve cyclic harvesting.

2. The algal biofilm harvesting method capable of reducing release of planktonic microalgae according to claim 1, wherein the biofilm is made of a silicone film.

3. The algal biofilm harvesting method capable of reducing release of planktonic microalgae according to claim 1, wherein a result obtained by dividing a length of the algal biofilm by a length of the cutting unit is an integer, and a result obtained by dividing a width of the algal biofilm by a width of the cutting unit is an integer, and the total number n of cuts is greater than or equal to 60 and less than or equal to 375.

4. The algal biofilm harvesting method capable of reducing release of planktonic microalgae according to claim 1, wherein a length-width ratio of the algal biofilm is 3:2 or 5:3.

5. The algal biofilm harvesting method capable of reducing release of planktonic microalgae according to claim 1, wherein the number $n_d$ of cutting units cut per day in step S2 is an integer, and the harvest cycle $\Delta t$ is greater than or equal to 7 d and less than or equal to 60 d.

6. The algal biofilm harvesting method capable of reducing release of planktonic microalgae according to claim 1, wherein each algal biofilm treatment system in the sewage tank is configured to harvest the microalgae biomass independently and synchronously according to steps in S3-1 to S3-5.

7. The algal biofilm harvesting method capable of reducing release of planktonic microalgae according to claim 1, wherein in step S3, the microalgae biomass is harvested by a scraper or hydraulic cutting.

* * * * *